(12) United States Patent
Rothstein et al.

(10) Patent No.: US 6,683,168 B1
(45) Date of Patent: Jan. 27, 2004

(54) GENES AND METHODS THAT MODULATE APOPTOSIS

(75) Inventors: Thomas L. Rothstein, Newton, MA (US); Thomas J. Schneider, Walpole, MA (US); Terrence J. Donohoe, East Boston, MA (US)

(73) Assignee: Boston Medical Center Corporation, Boston, MA (US)

( * ) Notice: Subject to any disclaimer, the term of this patent is extended or adjusted under 35 U.S.C. 154(b) by 0 days.

(21) Appl. No.: 09/687,363

(22) Filed: Oct. 13, 2000

Related U.S. Application Data

(63) Continuation of application No. PCT/US99/08658, filed on Apr. 20, 1999.
(60) Provisional application No. 60/124,805, filed on Mar. 15, 1999, and provisional application No. 60/082,503, filed on Apr. 21, 1998.

(51) Int. Cl.[7] .............................................. C07H 21/04
(52) U.S. Cl. ................ 536/23.5; 536/24.33; 435/320.1; 435/325
(58) Field of Search ............................. 536/23.5, 24.33; 435/320.1, 325

(56) References Cited

FOREIGN PATENT DOCUMENTS

WO      WO-9953743 A2 * 10/1999

OTHER PUBLICATIONS

Rothstein TL, et al. Immunol Rev Aug. 2000; 176: 116–33.*
Zhong X, et al. Mol Immunol Jan. 2001; 38 (1): 65–72.*
Hillier, L, et al, 1997, Database Genbank Accession No. AA477027, zu38b09.r1 Soares ovary tumor NbHOT Homo sapiens cDNA clone IMAGE:740249 5', mRNA sequence.*
Bonaldo, MF, et al, 1996, Genome Research, vol. 9, No. 9, pp. 791–806 (Database GenBank Accession No. BE112969).*
Hillier, L, et al, 1996, Genome Research, vol. 6, No. 9, pp. 807–828 (Database GenBank Accession No. AA099194).*
NCI–CGAP, 1997, Database GenBank Accession No. AW118945, xd98g05.x1 Soares_NFL_T_GBC_S1 *Homo sapiens* cDNA clone IMAGE:2605688 3'similar to WP:C44B11.1 CE08695; mRNA sequence.*
Schneider, T., et al., J. Exp. Med. 189: 949–955 (1999).
Rothstein, T., et al., Nature 374: 163–165 (1995).
Rathmell, et al., Cell 87: 319–329 (1996).
Lagresle, et al., J. Exp. Med. 183: 1377–1388 (1996).
Foote, et al., J. Immunol. 157: 1878–1885 (1996).
Schneider, T., et al., J. Immunol. 159: 4384–4389 (1997).

* cited by examiner

*Primary Examiner*—Anthony C. Caputa
*Assistant Examiner*—Stephen L. Rawlings
(74) *Attorney, Agent, or Firm*—Nixon Peabody LLP

(57) ABSTRACT

This invention generally relates to the nucleic acid sequences of a novel gene FAIM that encodes an apoptosis inhibiting protein. Furthermore, this invention relates to methods of identifying and testing antagonists of FAIM activity and screening for inter- and intra-specific homologs and mutants of FAIM.

5 Claims, 15 Drawing Sheets

Figure 2A

Human faim short DNA sequence

```
ATGACAGATCTCGTAGCTGTTTGGGATGTTGCTTTAAGTGACGGAGTCCACAAGATC
GAATTTGAACATGGGACTACATCAGGCAAACGAGTAGTATATGTAGATGGAAAGGA
AGAGATAAGAAAAGAGTGGATGTTCAAATTAGTGGGCAAAGAAACATTCTATGTTG
GAGCTGCAAAGACAAAAGCGACCATAAATATAGACGCTATCAGTGGTTTTGCTTAT
GAATATACTCTGGAAATTAATGGGAAAAGTCTCAAGAAGTATATGGAGGACAGATC
AAAAACCACCAATACTTGGGTATTACACATGGATGGTGAGAACTTTAGAATTGTTTT
GGAAAAAGATGCTATGGACGTATGGTGCAATGGTAAAAAATTGGAGACAGCGGGTG
AGTTTGTAGATGATGGGACTGAAACTCACTTCAGTATCGGGAACCATGACTGTTACA
TAAAGGCTGTCAGTAGTGGGAAGCGGAAGAAGGGATTATTCATACTCTCATTGTG
GATAATAGAGAAATCCCAGAGATTGCAAGTTAATGA
```

Figure 2B

Human faim short protein

MTDLVAVWDVALSDGVHKIEFEHGTTSGKRVVYVDGKEEIRKEWMFKLVGKETFYVG
AAKTKATINIDAISGFAYEYTLEINGKSLKKYMEDRSKTTNTWVLHMDGENFRIVLEKD
AMDVWCNGKKLETAGEFVDDGTETHFSIGNHDCYIKAVSSGKRKEGIIHTLIVDNREIPE
IAS

Figure 2C

>Human faim long DNA sequence

ATGGCATCTGGAGATGACAGTCCTATCTTTGAAGATGATGAAAGCCCTCCTTACAGC
CTAGAAAAAATGACAGATCTCGTAGCTGTTTGGGATGTTGCTTTAAGTGACGGAGTC
CACAAGATCGAATTTGAACATGGGACTACATCAGGCAAACGAGTAGTATATGTAGA
TGGAAAGGAAGAGATAAGAAAAGAGTGGATGTTCAAATTAGTGGGCAAAGAAACA
TTCTATGTTGGAGCTGCAAAGACAAAAGCGACCATAAATATAGACGCTATCAGTGG
TTTTGCTTATGAATATACTCTGGAAATTAATGGGAAAAGTCTCAAGAAGTATATGGA
GGACAGATCAAAAACCACCAATACTTGGGTATTACACATGGATGGTGAGAACTTTA
GAATTGTTTTGGAAAAAGATGCTATGGACGTATGGTGCAATGGTAAAAAATTGGAG
ACAGCGGGTGAGTTTGTAGATGATGGGACTGAAACTCACTTCAGTATCGGGAACCA
TGACTGTTACATAAAGGCTGTCAGTAGTGGGAAGCGGAAAGAAGGGATTATTCATA
CTCTCATTGTGGATAATAGAGAAATCCCAGAGATTGCAAGTTAA

Figure 2D human faim long protein

MASGDDSPIFEDDESPPYSLEKMTDLVAVWDVALSDGVHKIEFEHGTTSGKRVVYVDG
KEEIRKEWMFKLVGKETFYVGAAKTKATINIDAISGFAYEYTLEINGKSLKKYMEDRSK
TTNTWVLHMDGENFRIVLEKDAMDVWCNGKKLETAGEFVDDGTETHFSIGNHDCYIK
AVSSGKRKEGIIHTLIVDNREIPEIAS

Figure 2E human faim super long dna sequence

ATGCGCGGAGGGTGCGGCCTTCGGCTGAGGCAGAGGACCAGGGTTGGGTCCGTGGC
GGCGGGAGGGGTGGCCTCCTGCGCTGGTCGCCCCAGGGGACCTGAGAGGCGCGACA
AACAGTCGGCGCGTTTGGTACTCGCGCCTGCAGAGCTTTCAACCTCCGCGCCGGCTG
CCTGGTNTTCTCGGCCAGGGGAGCAAGGCCACGCGGCTANCGCAGCCGAGTCGGAA
CCAACCGGTTGTTTGGTGAAACTACCCCAGAGCCTCCCGCGGCCCACAGAGCACAGC
CCTCCTTACAGCCTAGAAAAAATGACAGATCTCGTAGCTGTTTGGGATGTTGCTTTA
AGTGACGGAGTCCACAAGATCGAATTTGAACATGGGACTACATCAGGCAAACGAGT
AGTATATGTAGATGGAAAGGAAGAGATAAGAAAAGAGTGGATGTTCAAATTAGTGG
GCAAAGAAACATTCTATGTTGGAGCTGCAAAGACAAAAGCGACCATAAATATAGAC
GCTATCAGTGGTTTTGCTTATGAATATACTCTGGAAATTAATGGGAAAAGTCTCAAG
AAGTATATGGAGGACAGATCAAAAACCACCAATACTTGGGTATTACACATGGATGG
TGAGAACTTTAGAATTGTTTTGGAAAAAGATGCTATGGACGTATGGTGCAATGGTAA
AAAATTGGAGACAGCGGGTGAGTTTGTAGATGATGGGACTGAAACTCACTTCAGTA
TCGGGAACCATGACTGTTACATAAAGGCTGTCAGTAGTGGGAAGCGGAAAGAAGGG
ATTATTCATACTCTCATTGTGGATAATAGAGAAATCCCAGAGATTGCAAGTTAATGA

Figure 2F human faim super long protein

MRGGCGLRLRQRTRVGSVAAGGVASCAGRPRGPERRDKQSARLVLAPAELSTSAPAA
WXSRPGEQGHAAXAAESEPTGCLVKLPQSLPRPTEHSPPYSLEKMTDLVAVWDVALSD
GVHKIEFEHGTTSGKRVVYVDGKEEIRKEWMFKLVGKETFYVGAAKTKATINIDAISGF
AYEYTLEINGKSLKKYMEDRSKTTNTWVLHMDGENFRIVLEKDAMDVWCNGKKLETA
GEFVDDGTETHFSIGNHDCYIKAVSSGKRKEGIIHTLIVDNREIPEIAS

Figure 2G human faim lung cancer DNA sequence

ATGGCATCTGGAGATGACAGTCCTATCTTTGAAGATGATGAAAGCCCTCCTTACAGC
CTAGAAAAAATGACAGATCTCGTAGCTGTTTGGGATGTTGCTTTAAGTGACGGAGTC
CACAAGATCGAATTTGAACATGGGACTACATCAGGCAAACGAGTAGTATATGTAGA
TGGAAAGGAAAAAGATGCTATGGACGTATGGTGCAATGGTAAAAAATTGGAGACAG
CGGGTGAGTTTGTAGATGATGGGACTGAAACTCACTTCAGTATCGGGAACCATGACT
GTTACATAAAGGCTGTCAGTAGTGGGAAGCGGAAAGAAGGGATTATTCATACTCTC
ATTGTGGATAATAGAGAAATCCCAGAGATTGCAAGTTAATGA

Figure 2H human faim lung cancer protein

MASGDDSPIFEDDESPPYSLEKMTDLVAVWDVALSDGXHKIEFEHGTTSGKRVVYVDG
KEKDAMDVWCNGKKLETAGEFVDDGTETHFSIGNHDCYIKAVSSGKRKEGIIHTLIVDN
REIPEIAS

Figure 2I murine faim short DNA sequence

ATGACGGATCTCGTAGCTGTTTGGGACGTAGCATTAAGTGACGGAGTCCACAAGATT
GAATTTGAACATGGGACCACATCAGGCAAGCGGGTTGTGTACGTGGATGGGAAGGA
AGAGATAAGAAGAGAGTGGATGTTCAAGTTGGTGGGCAAAGAAACGTTCTTTGTCG
GAGCTGCAAAAACCAAAGCCACCATCAATATAGATGCCATAAGTGGCTTCGCATAC
GAGTACACGCTGGAAATTGATGGGAAGAGCCTCAAGAAGTACATGGAGAACAGGTC
AAAGACCACCAGCACCTGGGTGCTGCGCCTGGATGGCGAGGACCTGAGAGTTGTTTT
GGAAAAAGACACTATGGACGTATGGTGCAATGGTCAGAAAATGGAGACAGCGGGC
GAGTTTGTAGATGATGGGACTGAGACGCACTTCAGCGTTGGGAACCACGGCTGTTAC
ATAAAAGCTGTGAGCAGCGGAAAGAGGAAAGAAGGGATTATCCATACCCTCATTGT
GGATAACAGGGAAATCCCAGAGCTCACTCAGTGA

Figure 2J

Murine FAIM short protein

MTDLVAVWDVALSDGVHKIEFEHGTTSGKRVVYVDGKEEIRREWMFKLVGKETFFVG
AAKTKATINIDAISAFAYEYTLEIDGKSLKKYMENRSKTTSTWVLRLDGEDLRVVLEKD
TMDVWCNGQKMETAGEFVDDGTETHFSVGNHGCYIKAVSSGKRKEGIIHTLIVDNREIP
ELTQ

Figure 2K

Murine Faim long DNA sequence

ATGGCGTCTGGAGATGACAGTCCTATCTTTGAAGATGATGAAAGCCCTCTCTATAGC
CTGGAAAAAATGACGGATCTCGTAGCTGTTTGGGACGTAGCATTAAGTGACGGAGT
CCACAAGATTGAATTTGAACATGGGACCACATCAGGCAAGCGGGTTGTGTACGTGG
ATGGGAAGGAAGAGATAAGAAGAGAGTGGATGTTCAAGTTGGTGGGCAAAGAAAC
GTTCTTTGTCGGAGCTGCAAAAACCAAAGCCACCATCAATATAGATGCCATAAGTGG
CTTCGCATACGAGTACACGCTGGAAATTGATGGGAAGAGCCTCAAGAAGTACATGG
AGAACAGGTCAAAGACCACCAGCACCTGGGTGCTGCGCCTGGATGGCGAGGACCTG
AGAGTTGTTTTGGAAAAAGACACTATGGACGTATGGTGCAATGGTCAGAAAATGGA
GACAGCGGGCGAGTTTGTAGATGATGGGACTGAGACGCACTTCAGCGTTGGGAACC
ACGGCTGTTACATAAAAGCTGTGAGCAGCGGAAAGAGGAAAGAAGGGATTATCCAT
ACCCTCATTGTGGATAACAGGGAAATCCCAGAGCTCACTCAGTGA

Figure 2L

Murine faim long protein

MASGDDSPIFEDDESPLYSLEKMTDLVAVWDVALSDGVHKIEFEHGTTSGKRVVYVDG
KEEIRREWMFKLVGKETFFVGAAKTKATINIDAISGFAYEYTLEIDGKSLKKYMENRSK
TTSTWVLRLDGEDLRVVLEKDTMDVWCNGQKMETAGEFVDDGTETHFSVGNHGCYIK
AVSSGKRKEGIIHTLIVDNREIPELTQ

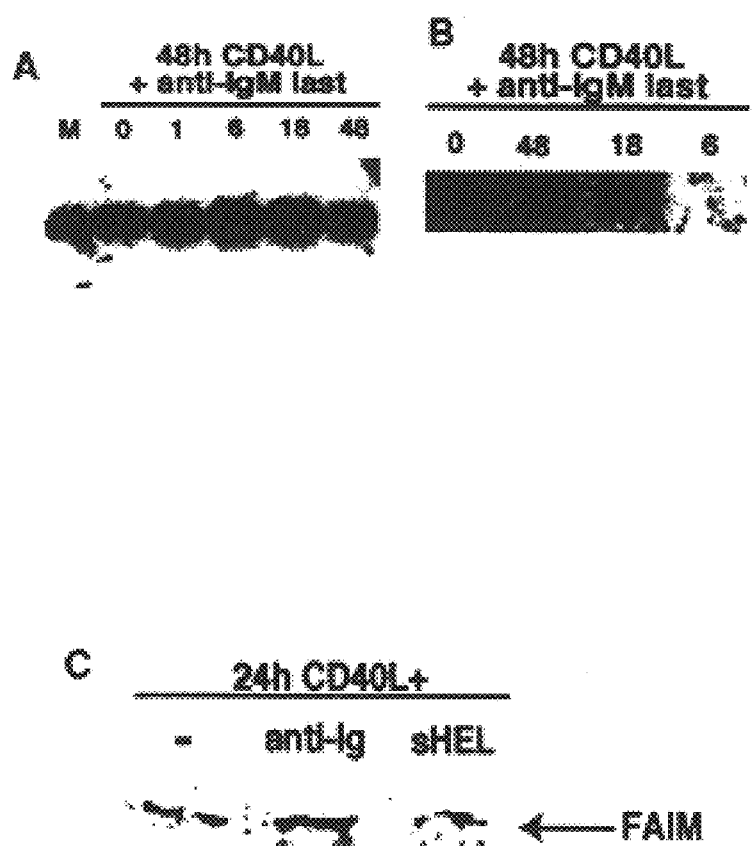

SEQUENCE LISTING

<160> NUMBER OF SEQ ID NOS: 12

<210> SEQ ID NO 1
<211> LENGTH: 543
<212> TYPE: DNA
<213> ORGANISM: Homo sapiens

<400> SEQUENCE: 1

```
atgacagatc tcgtagctgt ttgggatgtt gctttaagtg acggagtcca caagatcgaa      60
tttgaacatg ggactacatc aggcaaacga gtagtatatg tagatggaaa ggaagagata     120
agaaaagagt ggatgttcaa attagtgggc aaagaaacat tctatgttgg agctgcaaag     180
acaaaagcga ccataaatat agacgctatc agtggttttg cttatgaata tactctggaa     240
attaatggga aaagtctcaa gaagtatatg gaggacagat caaaaaccac caatacttgg     300
gtattacaca tggatggtga aactttaga attgttttgg aaaaagatgc tatggacgta     360
tggtgcaatg gtaaaaaatt ggagacagcg ggtgagtttg tagatgatgg gactgaaact     420
cacttcagta tcgggaacca tgactgttac ataaaggctg tcagtagtgg aagcggaaa      480
gaagggatta ttcatactct cattgtggat aatagagaaa tcccagagat tgcaagttaa     540
tga                                                                    543
```

<210> SEQ ID NO 2
<211> LENGTH: 179
<212> TYPE: PRT
<213> ORGANISM: Homo sapiens

<400> SEQUENCE: 2

```
Met Thr Asp Leu Val Ala Val Trp Asp Val Ala Leu Ser Asp Gly Val
1               5                   10                  15

His Lys Ile Glu Phe Glu His Gly Thr Thr Ser Gly Lys Arg Val Val
            20                  25                  30

Tyr Val Asp Gly Lys Glu Glu Ile Arg Lys Glu Trp Met Phe Lys Leu
        35                  40                  45

Val Gly Lys Glu Thr Phe Tyr Val Gly Ala Ala Lys Thr Lys Ala Thr
    50                  55                  60

Ile Asn Ile Asp Ala Ile Ser Gly Phe Ala Tyr Glu Tyr Thr Leu Glu
65                  70                  75                  80

Ile Asn Gly Lys Ser Leu Lys Lys Tyr Met Glu Asp Arg Ser Lys Thr
                85                  90                  95

Thr Asn Thr Trp Val Leu His Met Asp Gly Glu Asn Phe Arg Ile Val
            100                 105                 110

Leu Glu Lys Asp Ala Met Asp Val Trp Cys Asn Gly Lys Lys Leu Glu
        115                 120                 125

Thr Ala Gly Glu Phe Val Asp Asp Gly Thr Glu Thr His Phe Ser Ile
    130                 135                 140

Gly Asn His Asp Cys Tyr Ile Lys Ala Val Ser Ser Gly Lys Arg Lys
145                 150                 155                 160

Glu Gly Ile Ile His Thr Leu Ile Val Asp Asn Arg Glu Ile Pro Glu
                165                 170                 175

Ile Ala Ser
```

<210> SEQ ID NO 3
<211> LENGTH: 606
<212> TYPE: DNA

<213> ORGANISM: Homo sapiens

<400> SEQUENCE: 3

| | | | | | |
|---|---|---|---|---|---|
| atggcatctg | agatgacag | tcctatcttt | gaagatgatg | aaagccctcc | ttacagccta | 60 |
| gaaaaaatga | cagatctcgt | agctgtttgg | gatgttgctt | taagtgacgg | agtccacaag | 120 |
| atcgaatttg | aacatggac | tacatcaggc | aaacgagtag | tatatgtaga | tggaaaggaa | 180 |
| gagataagaa | aagagtggat | gttcaaatta | gtgggcaaag | aaacattcta | tgttggagct | 240 |
| gcaaagacaa | aagcgaccat | aaatatagac | gctatcagtg | gttttgctta | tgaatatact | 300 |
| ctggaaatta | atgggaaaag | tctcaagaag | tatatggagg | acagatcaaa | aaccaccaat | 360 |
| acttgggtat | tacacatgga | tggtgagaac | tttagaattg | ttttggaaaa | agatgctatg | 420 |
| gacgtatggt | gcaatggtaa | aaaattggag | acagcgggtg | agtttgtaga | tgatgggact | 480 |
| gaaactcact | tcagtatcgg | gaaccatgac | tgttacataa | aggctgtcag | tagtgggaag | 540 |
| cggaaagaag | ggattattca | tactctcatt | gtggataata | gagaaatccc | agagattgca | 600 |
| agttaa | | | | | | 606 |

<210> SEQ ID NO 4
<211> LENGTH: 201
<212> TYPE: PRT
<213> ORGANISM: Homo sapiens

<400> SEQUENCE: 4

Met Ala Ser Gly Asp Asp Ser Pro Ile Phe Glu Asp Asp Glu Ser Pro
1               5                   10                  15

Pro Tyr Ser Leu Glu Lys Met Thr Asp Leu Val Ala Val Trp Asp Val
            20                  25                  30

Ala Leu Ser Asp Gly Val His Lys Ile Glu Phe Glu His Gly Thr Thr
        35                  40                  45

Ser Gly Lys Arg Val Val Tyr Val Asp Gly Lys Glu Glu Ile Arg Lys
    50                  55                  60

Glu Trp Met Phe Lys Leu Val Gly Lys Glu Thr Phe Tyr Val Gly Ala
65                  70                  75                  80

Ala Lys Thr Lys Ala Thr Ile Asn Ile Asp Ala Ile Ser Gly Phe Ala
                85                  90                  95

Tyr Glu Tyr Thr Leu Glu Ile Asn Gly Lys Ser Leu Lys Lys Tyr Met
            100                 105                 110

Glu Asp Arg Ser Lys Thr Thr Asn Thr Trp Val Leu His Met Asp Gly
        115                 120                 125

Glu Asn Phe Arg Ile Val Leu Glu Lys Asp Ala Met Asp Val Trp Cys
    130                 135                 140

Asn Gly Lys Lys Leu Glu Thr Ala Gly Glu Phe Val Asp Asp Gly Thr
145                 150                 155                 160

Glu Thr His Phe Ser Ile Gly Asn His Asp Cys Tyr Ile Lys Ala Val
                165                 170                 175

Ser Ser Gly Lys Arg Lys Glu Gly Ile Ile His Thr Leu Ile Val Asp
            180                 185                 190

Asn Arg Glu Ile Pro Glu Ile Ala Ser
        195                 200

<210> SEQ ID NO 5
<211> LENGTH: 846
<212> TYPE: DNA
<213> ORGANISM: Homo sapiens
<220> FEATURE:

<221> NAME/KEY: Unsure
<222> LOCATION: (176)(209)
<223> OTHER INFORMATION: Unsure

<400> SEQUENCE: 5

```
atgcgcggag ggtgcggcct tcggctgagg cagaggacca gggttgggtc cgtggcggcg    60
ggaggggtgg cctcctgcgc tggtcgcccc aggggacctg agaggcgcga caaacagtcg   120
gcgcgtttgg tactcgcgcc tgcagagctt tcaacctccg cgccggctgc ctggtnttct   180
cggccagggg agcaaggcca cgcggctanc gcagccgagt cggaaccaac cggttgtttg   240
gtgaaactac cccagagcct cccgcggccc acagagcaca gccctcctta cagcctagaa   300
aaaatgacag atctcgtagc tgtttgggat gttgctttaa gtgacggagt ccacaagatc   360
gaatttgaac atgggactac atcaggcaaa cgagtagtat atgtagatgg aaaggaagag   420
ataagaaaag agtggatgtt caaattagtg ggcaaagaaa cattctatgt tggagctgca   480
aagacaaaag cgaccataaa tatagacgct atcagtggtt ttgcttatga atatactctg   540
gaaattaatg ggaaaagtct caagaagtat atggaggaca gatcaaaaac caccaatact   600
tgggtattac acatggatgg tgagaacttt agaattgttt tggaaaaaga tgctatggac   660
gtatggtgca atggtaaaaa attggagaca gcgggtgagt ttgtagatga tgggactgaa   720
actcacttca gtatcgggaa ccatgactgt tacataaagg ctgtcagtag tgggaagcgg   780
aaagaaggga ttattcatac tctcattgtg gataatagag aaatcccaga gattgcaagt   840
taatga                                                              846
```

<210> SEQ ID NO 6
<211> LENGTH: 280
<212> TYPE: PRT
<213> ORGANISM: Homo sapiens
<220> FEATURE:
<221> NAME/KEY: Unsure
<222> LOCATION: (59)(70)
<223> OTHER INFORMATION: Unsure

<400> SEQUENCE: 6

```
Met Arg Gly Gly Cys Gly Leu Arg Leu Arg Gln Arg Thr Arg Val Gly
 1               5                  10                  15

Ser Val Ala Ala Gly Gly Val Ala Ser Cys Ala Gly Arg Pro Arg Gly
            20                  25                  30

Pro Glu Arg Arg Asp Lys Gln Ser Ala Arg Leu Val Leu Ala Pro Ala
        35                  40                  45

Glu Leu Ser Thr Ser Ala Pro Ala Ala Trp Xaa Ser Arg Pro Gly Glu
50                  55                  60

Gln Gly His Ala Ala Xaa Ala Ala Glu Ser Glu Pro Thr Gly Cys Leu
65                  70                  75                  80

Val Lys Leu Pro Gln Ser Leu Pro Arg Pro Thr Glu His Ser Pro Pro
                85                  90                  95

Tyr Ser Leu Glu Lys Met Thr Asp Leu Val Ala Val Trp Asp Val Ala
            100                 105                 110

Leu Ser Asp Gly Val His Lys Ile Glu Phe Glu His Gly Thr Thr Ser
        115                 120                 125

Gly Lys Arg Val Val Tyr Val Asp Gly Lys Glu Ile Arg Lys Glu
    130                 135                 140

Trp Met Phe Lys Leu Val Gly Lys Glu Thr Phe Tyr Val Gly Ala Ala
145                 150                 155                 160

Lys Thr Lys Ala Thr Ile Asn Ile Asp Ala Ile Ser Gly Phe Ala Tyr
```

|  |  |  |  | 165 |  |  |  | 170 |  |  |  | 175 |  |
|---|---|---|---|---|---|---|---|---|---|---|---|---|---|

Glu Tyr Thr Leu Glu Ile Asn Gly Lys Ser Leu Lys Tyr Met Glu
            180              185              190

Asp Arg Ser Lys Thr Thr Asn Thr Trp Val Leu His Met Asp Gly Glu
        195              200              205

Asn Phe Arg Ile Val Leu Glu Lys Asp Ala Met Asp Val Trp Cys Asn
        210              215              220

Gly Lys Lys Leu Glu Thr Ala Gly Glu Phe Val Asp Asp Gly Thr Glu
225              230              235              240

Thr His Phe Ser Ile Gly Asn His Asp Cys Tyr Ile Lys Ala Val Ser
            245              250              255

Ser Gly Lys Arg Lys Glu Gly Ile Ile His Thr Leu Ile Val Asp Asn
        260              265              270

Arg Glu Ile Pro Glu Ile Ala Ser
        275              280

<210> SEQ ID NO 7
<211> LENGTH: 381
<212> TYPE: DNA
<213> ORGANISM: Homo sapiens

<400> SEQUENCE: 7

```
atggcatctg gagatgacag tcctatcttt gaagatgatg aaagccctcc ttacagccta      60
gaaaaaatga cagatctcgt agctgtttgg gatgttgctt taagtgacgg agtccacaag     120
atcgaatttg aacatggac tacatcaggc aaacgagtag tatatgtaga tggaaaggaa     180
aaagatgcta tggacgtatg gtgcaatggt aaaaaattgg agacagcggg tgagtttgta     240
gatgatggga ctgaaactca cttcagtatc gggaaccatg actgttacat aaaggctgtc     300
agtagtggga agcggaaaga agggattatt catactctca ttgtggataa tagagaaatc     360
ccagagattg caagttaatg a                                               381
```

<210> SEQ ID NO 8
<211> LENGTH: 125
<212> TYPE: PRT
<213> ORGANISM: Homo sapiens
<220> FEATURE:
<221> NAME/KEY: Unsure
<222> LOCATION: (38)
<223> OTHER INFORMATION: Unsure

<400> SEQUENCE: 8

Met Ala Ser Gly Asp Asp Ser Pro Ile Phe Glu Asp Asp Glu Ser Pro
1              5                10              15

Pro Tyr Ser Leu Glu Lys Met Thr Asp Leu Val Ala Val Trp Asp Val
            20              25              30

Ala Leu Ser Asp Gly Xaa His Lys Ile Glu Phe Glu His Gly Thr Thr
        35              40              45

Ser Gly Lys Arg Val Val Tyr Val Asp Gly Lys Glu Lys Asp Ala Met
    50              55              60

Asp Val Trp Cys Asn Gly Lys Lys Leu Glu Thr Ala Gly Glu Phe Val
65              70              75              80

Asp Asp Gly Thr Glu Thr His Phe Ser Ile Gly Asn His Asp Cys Tyr
            85              90              95

Ile Lys Ala Val Ser Ser Gly Lys Arg Lys Glu Gly Ile Ile His Thr
            100             105            110

Leu Ile Val Asp Asn Arg Glu Ile Pro Glu Ile Ala Ser

-continued

```
                      115                 120                 125

<210> SEQ ID NO 9
<211> LENGTH: 541
<212> TYPE: DNA
<213> ORGANISM: Mouse

<400> SEQUENCE: 9
atgacggatc tcgtagctgt ttgggacgta gcattaagtg acggagtcca caagattgaa      60
tttgaacatg ggaccacatc aggcaagcgg gttgtgtacg tggatgggaa ggaagagata     120
agaagagagt ggatgttcaa gttggtgggc aaagaaacgt tctttgtcgg agctgcaaaa     180
accaaagcca ccatcaatat agatgccata agtggcttcg catacgagta cacgctggaa     240
attgatggga agagcctcaa gaagtacatg gagaacaggt caaagaccac cagcacctgg     300
gtgctgcgcc tggatggcga ggacctgaga gttgttttgg aaaaagacac tatggacgta     360
tggtgcaatg gtcagaaaat ggagacagcg ggcgagtttg tagatgatgg gactgagacg     420
cacttcagcg ttgggaacca cggctgttac ataaaagctg tgagcagcgg aaagaggaaa     480
gaagggatta tccataccct cattgtggga taacaggaa  atcccagagc tcactcagtg     540
a                                                                    541

<210> SEQ ID NO 10
<211> LENGTH: 179
<212> TYPE: PRT
<213> ORGANISM: Mouse

<400> SEQUENCE: 10

Met Thr Asp Leu Val Ala Val Trp Asp Val Ala Leu Ser Asp Gly Val
 1               5                  10                  15

His Lys Ile Glu Phe Glu His Gly Thr Thr Ser Gly Lys Arg Val Val
             20                  25                  30

Tyr Val Asp Gly Lys Glu Glu Ile Arg Arg Glu Trp Met Phe Lys Leu
         35                  40                  45

Val Gly Lys Glu Thr Phe Phe Val Gly Ala Ala Lys Thr Lys Ala Thr
     50                  55                  60

Ile Asn Ile Asp Ala Ile Ser Ala Phe Ala Tyr Glu Tyr Thr Leu Glu
65                  70                  75                  80

Ile Asp Gly Lys Ser Leu Lys Lys Tyr Met Glu Asn Arg Ser Lys Thr
                 85                  90                  95

Thr Ser Thr Trp Val Leu Arg Leu Asp Gly Glu Asp Leu Arg Val Val
            100                 105                 110

Leu Glu Lys Asp Thr Met Asp Val Trp Cys Asn Gly Gln Lys Met Glu
        115                 120                 125

Thr Ala Gly Glu Phe Val Asp Asp Gly Thr Glu Thr His Phe Ser Val
    130                 135                 140

Gly Asn His Gly Cys Tyr Ile Lys Ala Val Ser Ser Gly Lys Arg Lys
145                 150                 155                 160

Glu Gly Ile Ile His Thr Leu Ile Val Asp Asn Arg Glu Ile Pro Glu
                165                 170                 175

Leu Thr Gln

<210> SEQ ID NO 11
<211> LENGTH: 606
<212> TYPE: DNA
<213> ORGANISM: Mouse
```

```
<400> SEQUENCE: 11
atggcgtctg gagatgacag tcctatcttt gaagatgatg aaagccctct ctatagcctg      60
gaaaaaatga cggatctcgt agctgtttgg gacgtagcat taagtgacgg agtccacaag     120
attgaatttg aacatggac cacatcaggc aagcgggttg tgtacgtgga tgggaaggaa     180
```
(line 3 corrected to match image)
```
attgaatttg aacatgggac cacatcaggc aagcgggttg tgtacgtgga tgggaaggaa     180
gagataagaa gagagtggat gttcaagttg gtgggcaaag aaacgttctt tgtcggagct     240
gcaaaaacca agccaccat caatatagat gccataagtg cttcgcata cgagtacacg     300
```
(corrected)
```
gcaaaaacca agccaccat caatatagat gccataagtg cttcgcata cgagtacacg     300
```

```
<400> SEQUENCE: 11
atggcgtctg gagatgacag tcctatcttt gaagatgatg aaagccctct ctatagcctg      60
gaaaaaatga cggatctcgt agctgtttgg gacgtagcat taagtgacgg agtccacaag     120
attgaatttg aacatgggac cacatcaggc aagcgggttg tgtacgtgga tgggaaggaa     180
gagataagaa gagagtggat gttcaagttg gtgggcaaag aaacgttctt tgtcggagct     240
gcaaaaacca agccaccat caatatagat gccataagtg cttcgcata cgagtacacg     300
ctggaaattg atgggaagag cctcaagaag tacatggaga caggtcaaa gaccaccagc     360
acctgggtgc tgcgcctgga tgcgaggac ctgagagttg ttttggaaaa agacactatg     420
gacgtatggt gcaatggtca gaaatggag acagcgggcg agtttgtaga tgatgggact     480
gagacgcact tcagcgttgg gaaccacggc tgttacataa aagctgtgag cagcggaaag     540
aggaaagaag ggattatcca taccctcatt gtggataaca gggaaatccc agagctcact     600
cagtga                                                                606

<210> SEQ ID NO 12
<211> LENGTH: 201
<212> TYPE: PRT
<213> ORGANISM: Mouse

<400> SEQUENCE: 12

Met Ala Ser Gly Asp Asp Ser Pro Ile Phe Glu Asp Asp Glu Ser Pro
1               5                   10                  15

Leu Tyr Ser Leu Glu Lys Met Thr Asp Leu Val Ala Val Trp Asp Val
            20                  25                  30

Ala Leu Ser Asp Gly Val His Lys Ile Glu Phe Glu His Gly Thr Thr
        35                  40                  45

Ser Gly Lys Arg Val Val Tyr Val Asp Gly Lys Glu Ile Arg Arg
    50                  55                  60

Glu Trp Met Phe Lys Leu Val Gly Lys Glu Thr Phe Phe Val Gly Ala
65                  70                  75                  80

Ala Lys Thr Lys Ala Thr Ile Asn Ile Asp Ala Ile Ser Gly Phe Ala
                85                  90                  95

Tyr Glu Tyr Thr Leu Glu Ile Asp Gly Lys Ser Leu Lys Lys Tyr Met
            100                 105                 110

Glu Asn Arg Ser Lys Thr Thr Ser Thr Trp Val Leu Arg Leu Asp Gly
        115                 120                 125

Glu Asp Leu Arg Val Val Leu Glu Lys Asp Thr Met Asp Val Trp Cys
    130                 135                 140

Asn Gly Gln Lys Met Glu Thr Ala Gly Glu Phe Val Asp Asp Gly Thr
145                 150                 155                 160

Glu Thr His Phe Ser Val Gly Asn His Gly Cys Tyr Ile Lys Ala Val
                165                 170                 175

Ser Ser Gly Lys Arg Lys Glu Gly Ile Ile His Thr Leu Ile Val Asp
            180                 185                 190

Asn Arg Glu Ile Pro Glu Leu Thr Gln
        195                 200
```

GENES AND METHODS THAT MODULATE APOPTOSIS

The present application is a continuation of PCT/US99/08658 filed on Apr. 20, 1999 which designated the United States, which is now abandoned, and which claimed the benefit of U.S. Provisional Application Nos. 60/082,503, field Apr. 21, 1998 and 60/124,805, filed Mar. 15, 1999.

This work was supported by United States Public Health Service grant AI40181 awarded by the National Institutes of Health and a grant from the Arthritis Foundation, the United States government has certain rights in this invention.

FIELD OF THE INVENTION

This invention generally relates to the nucleic acid sequences of a novel gene called the Fas Apoptosis Inhibitory Molecule (faim) that encodes an apoptosis inhibiting protein. Furthermore, this invention relates to methods of identifying and testing antagonists of FAIM activity and to methods to assay for FAIM expression.

BACKGROUND OF THE INVENTION

Programmed cell death (PCD) is mediated by a process called apoptosis. Although the investigation of cell death is a relatively new field of study, it has become readily apparent that many disease states are manifested due to the aberrant control of programmed cell death. Recent evidence suggest that the failure of cells to undergo apoptotic cell death might be involved in the pathogenesis of a variety of human diseases including cancer, autoimmune diseases and viral infections. The understanding of survival pathways would be critical in disease states where excessive cell numbers, such as in various cancers, are the result of cell death rather than cell proliferation. The screening of potential therapeutics has been hindered by both a lack of understanding of the physiological basis of cell death and by a dearth of reagents specific for critical points in the cell death signaling pathways. Additionally, much work has focused on the delineation of the death-inducing pathway and reagents that may block it and not on pathways that prevent apoptosis or confer survival signals. What is needed are reagents and methodologies that allow for the identification and testing of agonists and antagonists of apoptosis inhibiting pathways or cell survival pathways.

SUMMARY OF THE INVENTION

The present invention generally relates to compositions and methods of identifying and testing FAIM pathway agonists and antagonists. The product of the gene faim is responsible for preventing apoptosis in Bal-17 B lymphoma cells and in various murine cells. When ectopically expressed, FAIM inhibits apoptosis. In addition, the invention relates to methods to identify other members of the FAIM signal pathway, methods to identify homologs of FAIM which are native to other tissue or cell types and methods to generate reagents derived from the invention. Additionally, the invention relates to methods to assay for FAIM expression in various cell types including, but not limited to, cancer cells, autoimmune cells and diseased cells.

The present invention is not limited by the method of the employed screen. In one embodiment, the present invention contemplates screening suspected compounds in a system utilizing transfected cell lines. In one embodiment the cells may be transfected transiently. In another embodiment the cells may be stably transfected. In yet another embodiment, transgenic animals may be generated with the transgene under the control of an inducible, tissue specific promotor.

The present invention may also be used to identify new constituents of the FAIM signaling pathway. In one embodiment antibodies generated to translation products of the invention may be used in immunoprecipitation experiments to isolate novel FAIM pathway constituents or natural mutations thereof. In another embodiment the invention may be used to generate fusion proteins that could be used to isolate novel FAIM pathway constituents or natural mutations thereof. In yet another embodiment screens may be conducted using the yeast two-hybrid system.

The present invention may also be used to identify new homologs of FAIM or natural mutations thereof. The present invention contemplates screening for homologs using standard molecular procedures. In one embodiment screens are conducted using Northern and Southern blotting.

The present invention may also be used to determine the expression level of FAIM in various cell types including, but not limited to, pathological cells. In one embodiment, assays are conducted using FAIM antibodies to precipitate expressed FAIM. In another embodiment, assays are conducted using PCR primers or oligonucleotides that recognize FAIM RNA. In yet another embodiment, assays are conducted using various blotting techniques such as, but not limited to. Northern, Southern and Western blotting. The adaptation of such assays to high throughput screening techniques is also contemplated by the present invention.

The present invention further provides a composition comprising DNA having an oligonucleotide sequence of SEQ ID NO:1, SEQ ID NO:2, SEQ ID NO:3, SEQ ID NO:4, SEQ ID NO:5, or SEQ ID NO:6, or portions thereof. The present invention further includes isolated RNA transcribed from any of the DNA sequences listed above, isolated protein translated from the RNA, and isolated antibodies produced from the proteins. The present invention further provides expression constructs comprising any of the above listed DNA and cells comprising said expression constructs.

The present invention also provides a method of screening a compound comprising: providing, in any order, cells containing a recombinant expression vector, wherein the vector comprises at least a portion of the oligonucleotide sequences SEQ ID NO:1, SEQ ID NO:2, SEQ ID NO:3, SEQ ID NO:4, SEQ ID NO:5, SEQ ID NO:6, or variants or homologs thereof, and a compound suspected of having the ability to alter FAIM activity; and contacting the cells with the compound. In preferred embodiments, the method further comprises the steps of detecting programmed cell death modulation effects of the compound; and/or detecting the appropriate marker if a reporter construct was utilized for detection of compound interaction.

The present invention further provides a method of screening for homologs, said method comprising: providing, in any order 1) DNA, wherein DNA comprises at least a portion of the oligonucleotide sequences SEQ ID NO:1, SEQ ID NO:2, SEQ ID NO:3, SEQ ID NO:4, SEQ ID NO:5, or SEQ ID NO:6, or variants or homologs thereof, and 2) DNA libraries from cells or tissues suspected of having the homologs; and contacting the first DNA with the second DNA; and isolating, purifying, and sequencing the DNA suspected of coding for the homologs.

The present invention also provides methods of screening for interactive peptides, said method comprising: providing, in any order, 1) peptides, wherein the peptide comprises at least a portion of a peptide sequence of an isolated protein translated from RNA which is transcribed from the oligonucleotide sequences SEQ ID NO:1, SEQ ID NO:2, SEQ ID NO:3, SEQ ID NO:4, SEQ ID NO:5, or SEQ ID NO:6, or variants or homologs thereof, wherein the peptide has been modified with a GST or other suitable fusion protein for purification purposes, and 2) extracts from cells or tissues suspected of having the homolog; and contacting the extracts with the peptides; and isolating, purifying, and sequencing the homolog.

The present invention also provides methods of assaying for FAIM activity, said method comprising: providing, in any order, 1) antibodies produced from proteins translated from RNA which is transcribed from the oligonucleotide sequences SEQ ID NO:1, SEQ ID NO:2, SEQ ID NO:3, SEQ ID NO:4, SEQ ID NO:5, or SEQ ID NO:6, or variants or homologs thereof, and 2) extracts from cells suspected of expressing FAIM; contacting said extracts with said antibodies; and detecting said expressed FAIM.

DESCRIPTION OF THE FIGURES

FIG. 2A shows the nucleic acid sequence of short Human faim (SEQ ID NO:1).

FIG. 2B shows the amino acid sequence of short Human FAIM (SEQ ID NO:2).

FIG. 2C shows the nucleic acid sequence of long Human faim (SEQ ID NO:3).

FIG. 2D shows the amino acid sequence of long Human FAIM (SEQ ID NO:4).

FIG. 2E shows the nucleic acid sequence of super long Human faim (SEQ ID NO:5).

FIG. 2F shows the amino acid sequence super long Human FAIM (SEQ ID NO:6).

FIG. 2G shows the nucleic acid sequence of Human faim from lung cancer (SEQ ID NO:7).

FIG. 2H shows the amino acid sequence of Human FAIM from lung cancer (SEQ ID NO:8).

FIG. 2I shows the nucleic acid sequence of short Murine faim (SEQ ID NO:9).

FIG. 2J shows the amino acid sequence short Murine FAIM (SEQ ID NO:10).

FIG. 2K shows the nucleic acid sequence of long Murine faim (SEQ ID NO:11).

FIG. 2L shows the amino acid sequence long Murine FAIM (SEQ ID NO:12).

FIG. 4. Expression of faim/FAIM in Fas-resistant primary B cells. (A) Northern blot showing faim gene expression in primary B cells that were unstimulated by CD40L alone for 48 h (O), or were stimulated by CD40L for 48 h plus anti-Ig added for the last 1, 6, 18 or 48 h of culture, as indicated. (B) Western blot showing FAIM protein expression in primary B cells that were stimulated by CD40L alone for 48 h (O) or were stimulated by CD40L for 48 h plus anti-Ig added for the last 6, 18 or 48 h of culture, as indicated. (C) Western blot showing FAIM protein expression in primary B cells from double transgenic, anti-HEL/HEL mice that were stimulated by CD40L alone for 24 h (−) or were stimulated by CD40L in combination with either anti-Ig or sHEL, as indicated.

DEFINITIONS

Figure 1:
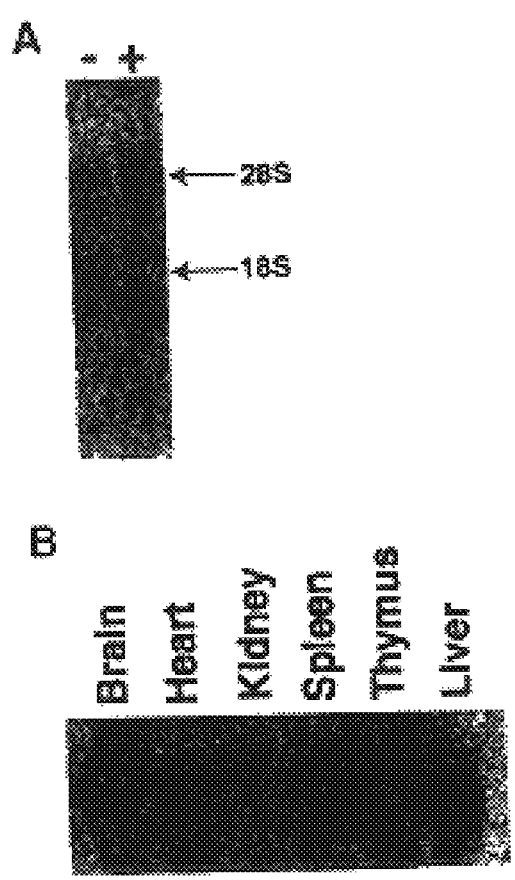
FIGS. 1. 1A shows differential expression via Northern blot of genes suspected of rendering B cells Fas resistant. 1B shows a Northern blot of expression of an RNA species in various murine tissues, as indicated in the figure.

To facilitate understanding of the invention, a number of terms are, defined below.

"Apoptosis" shall be defined as the generally recognized term for the morphological changes that are observed in a cell as the cell undergoes a non-accidental death.

"Programmed cell death" shall be defined as the term to describe the genetically controlled process that is executed in a cell that has been induced to undergo apoptosis.

"Gain of function" (gof) shall be defined as all modifications to an oligonucleotide that, when that oligonucleotide is transfected into a host organism and translated into a peptide, that peptide will function with increased efficiency as compared to the wild type peptide when the gene or gene product is induced to function whether that induction be continuous or non-continuous. It may, in effect, function as an augmenter of the natural gene if the natural gene is present and functional in the host into which the gof oligonucleotide was transfected, or it may add that function to the host if the natural gene is not present or is non-functional.

"Loss of function" (lof) shall be defined as all modifications to an oligonucleotide that, when that oligonucleotide is transfected into a host organism and translated into a peptide, that peptide will function with decreased efficiency as compared to the wild type peptide when the gene or gene product is induced to function whether that induction be continuous or non-continuous. It may, in effect, function as a diminisher of natural gene function if the natural gene is present and functional in the host into which the lof oligonucleotide was transfected, or may negatively interfere with processes in the host if the natural gene is not present or is non-functional.

"Antibody" shall be defined as a glycoprotein produced by B cells that binds with high specificity to the agent (usually, but not always, a peptide), or a structurally similar agent, that generated its production. Antibodies may be produced by any of the known methodologies (reference) and may be either polyclonal or monoclonal.

"Mutant" shall be defined as any changes made to a wild type nucleotide sequence, either naturally or artificially, that produces a translation product that functions with enhanced or decreased efficiency in at least one of a number of ways including, but not limited to, specificity for various interactive molecules, rate of reaction and longevity of the mutant molecule.

"Staining" shall be defined as any number of processes known to those in the field that are used to better visualize a specific component(s) and/or feature(s) of a cell or cells.

"TUNEL" shall be defined as terminal deoxynucleotidyl transferase (TdT)-mediated FITC-dUTP nick end labeling, a technique to quantitate apoptosis known to those in the field.

"Morphology" shall be defined as the visual appearance of a cell or organism when viewed with the eye, a light microscope or eletronmicroscope, as appropriate.

"Blebbing", in relation to cell morphology, shall be described as a ruffled appearance of the cell surface when the cell is viewed by either light or electron The term "gene" refers to a DNA sequence that comprises control and coding sequences necessary for the production of a polypeptide or its precursor. The polypeptide can be encoded by a full length coding sequence or by any portion of the coding sequence.

The term "nucleic acid sequence of interest" refers to any nucleic acid sequence the manipulation of which may be deemed desirable for any reason by one of ordinary skill in the art.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

As used herein, the terms "vector" and "vehicle" are used interchangeably in reference to nucleic acid molecules that transfer DNA segment(s) from once cell to another.

The term "expression construct", "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "in operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "hybridization" as used herein refers to any process by which a strand of nucleic acid joins with a complementary strand through base pairing.

As used herein, the terms "complementary" or "complementarity" when used in reference to polynucleotides refers to polynucleotides which are related by the base-pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g. less than about 30% identity); in the absence of non-specific binding the probe will not hybridize to the second non-complementary target.

Low stringency conditions when used in reference to nucleic acid hybridization comprise conditions equivalent to binding or hybridization at 42° C. in a solution consisting of 5X SSPE (43.8 g/l NaCl, 6.9 g/l $NaH_2PO_4 \cdot H_2O$ and 1.85 g/l EDTA, pH adjusted to 7.4 with NaOH), 0.1% SDS, 5X Denhardt's reagent [50X Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5X SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5X SSPE (43.8 g/l NaCl, 6.9 g/l $NaH_2PO_4 \cdot H_2O$ and 1.85 g/l EDTA, pH adjusted to 7.4 with NaOH), 0.5% SDS, 5X Denhardt's reagent and 100 µg/ml denatured salmon sperm DNA followed by washing in a solution comprising 0.1X SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

"Stringency" when used in reference to nucleic acid hybridization typically occurs in a range from about Thd m−5° C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. Under "stringent conditions" a nucleic acid sequence of interest will hybridize to its exact complement and closely related sequences.

As used herein, the term "fusion protein" refers to a chimeric protein containing the protein of interest (i.e., FAIM and fragments thereof) joined to an exogenous protein fragment (the fusion partner which consists of a non-FAIM sequence). The fusion partner may provide a detectable moiety, may provide an affinity tag to allow purification of the recombinant fusion protein from the host cell, or both. If desired, the fusion protein may be removed from the protein of interest by a variety of enzymatic or chemical means known to the art.

As used herein, the term "purified" or "to purify" refers to the removal of contaminants from a sample. The present invention contemplates purified compositions (discussed above).

As used herein the term "portion" when in reference to a protein (as in "a portion of a given protein") refers to fragments of that protein. The fragments may range in size from four amino acid residues to the entire amino acid sequence minus one amino acid. For immunization to generate antibodies, portions greater than ten (10) amino acids are preferred.

As used herein the term "portion" when in reference to nucleic acid refers to fragments of that nucliec acid. The fragments may range in size from oligonucleotides four bases in length to the entire nucleic acid sequence minus one base. For primers for use in PCR portions greater than ten (10) bases are preferred, and even more preferred are primers between twelve (12) and eighteen (18) bases. Such primers can be used to generate fragements by the PCR method, such fragments typically greater than 100 bases in length.

GENERAL DESCRIPTION OF THE INVENTION

The invention generally relates to compositions and methods of identifying and testing agonists and antagonists of FAIM activation. Additionally, the invention relates to methodologies made possible by the invention to identify new constituents of the cell death process and for the design of drugs, drug therapies and gene therapies that modify the programmed cell death process.

In vivo activation or ectopic expression of FAIM inhibits the apoptotic death of the cell in question. Expression of faim is associated with the reduction of Fas-induced poly-ADP-ribose polymerase (PARP) cleavage, a late stage indicator of apoptosis. Additionally, the gene sequence for faim is not homologuous to any other known gene sequence.

A. Measurement Of Apoptosis—General Indicators

Programmed cell death, or apoptosis, is the genetically controlled, systematic dismantling of a cell. Apoptosis typically happens during embryogenesis when much tissue remodeling is taking place, but continues to happen throughout the life of an organism. For example, the elimination of senescent cells, the involution of tissues and the elimination of diseased cells happens by apoptosis. The hallmarks of the apoptotic process are morphological changes consisting of chromatin condensation, membrane blebbing, loss of membrane integrity and, ultimately, the disintegration of the cell into apoptotic bodies that are engulfed by phagocytic cells. On the molecular scale, DNA is cleaved into 180–200 kb nucleosomal fragments resulting in a laddering appearance when run on an agarose gel. Apoptosis prevents the release of cellular constituents into the extracellular space thereby preventing an inflammatory response and allows for the orderly remodeling of tissues. (In contrast, necrotic or accidental cell death is exemplified by membrane rupture and the release of cellular constituents into the extracellular space resulting in an inflammatory response by the body).

Traditionally, the measurement of apoptosis has been concerned with the accuracy of delineating the percentage of a population undergoing apoptosis, with determining the earliest detectable point in which apoptosis could be accurately detected or with determining the kinetics of the apoptotic process. The changes in cellular morphology and the DNA laddering discussed above, although not overly quantitative, are the classic determinants of apoptosis. Other measures of apoptosis include, but are not limited to, terminal deoxynucleotidyl transferase (TdT)-mediated FITC-dUTP nick end labeling (TUNEL) staining (indicative of early DNA strand cutting by endonucleases), trypan blue staining (and various other vital stains indicative of loss of membrane integrity), propidium iodide (and various other DNA intercalating dyes indicative of loss of DNA from the nucleus) and Annexin-V staining (indicative of phosphatidyl serine exposure on the cell surface). These techniques allow for better quantitative analysis of apoptosis on a population level but do little to allow for the measurement of the effect of agonists or antagonists on a specific apoptotic signaling pathway.

B. Measurement of Apoptosis—Cell Pathway Specific Techniques

Some advances have been made into delineating pathway involvement in the apoptotic process. In this regard, inhibitors have been made which target some constituents of the apoptotic pathway. For example, tetra-peptide inhibitors have been developed for several of the caspases activated during apoptosis. Likewise, loss of function and gain of function gene mutants have been made for several steps in the apoptotic process. Additionally, reagents have been developed which combine a fluorogenic substrate with caspase cleavage sites allowing for the visualization of apoptosis-induced caspase activation by flow cytometric methods. These reagents, however, focus on the pro-apoptotic pathways and fail to look at survival pathways.

C. Modulation of B Cell Apoptosis

It has been shown that the susceptibility of primary B cells to Fas-mediated apoptosis is regulated in a receptor-specific fashion (Rothstein et al. "Protection against Fas-dependent Th-l-mediated apoptosis by antigen receptor engagement in B cells" *Nature* 374:163–165, 1995: Rathmell et al. "Expansion or elimination of B cells in vivo: dual roles for CD40- and Fas (CD95)-ligands modulated by the B cell antigen receptor" *Cell* 87:319–329, 1996; Lagresle et al. "Concurrent engagement of CD40 and the antigen receptor protects naive and memory human B cells from APO-1/Fas-mediated apoptosis" *J. Exp. Med.* 183:1377–1388, 1996). Engagement of CD40 upregulates Fas expression and renders B cells sensitive to Fas-mediated apoptosis, whereas concurrent or sequential signaling through the B cell antigen receptor induces a state of Fas resistance (Rothstein et al. "Protection against Fas-dependent Th-1-mediated apoptosis by antigen receptor engagement in B cells "Nature 374:163–165, 1995). Induction of Fas resistance develops progressively over a period of hours, and depends on macromolecular synthesis, suggesting that protection against Fas killing requires the induction and accumulation of one or more gene products (Foote et al. "Intracellular signaling for inducible antigen receptor-mediated Fas resistance in B cells" *J. Immunol.* 157:1878–1885, 1996). Indeed, it has recently demonstrated that Bcl-$x_L$ expression is upregulated in primary B cells that have been rendered Fas resistant, and showed that overexpression of Bcl-$x_L$ diminishes Fas-mediated apoptosis in CD40L-stimulated B cells obtained from transgenic mice (Schneider et al. "Bcl-x protects primary B cells against Fas-mediated apoptosis" *J. Immunol.* 159:4384–4389, 1997). However, a role for other gene products in suggested by three observations. First, Bcl-$x_L$-overexpressing B cells were not completely protected from Fas killing (Schneider et al. "Bcl-x protects primary B cells against Fas-mediated apoptosis" *J. Immunol.* 159:4384–4389, 1997). Second, treatment of Bcl-$x_L$-overexpressing B cells with anti-Ig produced additional inhibition of Fas-mediated apoptosis (Schneider et al. "Bcl-x protects primary B cells against Fas-mediated apoptosis" *J. Immunol.* 159:4384–4389, 1997). Third, Bcl-$x_L$ protein appeared in normal B cells after, not before, the first manifestation of anti-Ig-induced Fas resistance (Foote et al. "Intracellular signaling for inducible antigen receptor-mediated Fas resistance in B cells" *J. Immunol.* 157:1878–1885, 1996; Schneider et al. "Bcl-x protects primary B cells against Fas-mediated apoptosis" *J. Immunol.* 159:4384–4389, 1997). These results raise the possibility that additional gene products, induced by sIg crosslinking, contribute to Fas resistance. Hence, differential display was used to elucidate, in an unbiased and empirical fashion, inducible factors that modulate susceptibility to Fas-mediated apoptosis in B cells, and identified a gene that, when overexpressed in a model b cell line, reduces Fas sensitivity. We have called this novel gene Fas Apoptosis Inhibitory Molecule (faim).

D. Advances Conferred By The Present Invention

The invention will be used for, among other things, (1) the design and execution of screens to identify protein or small molecules that interfere with or augment the inhibition of apoptosis by FAIM: (2) the designing and execution of screens to identify and clone genes that are directly involved in FAIM signaling pathways; (3) the identification of new genes that regulate cell survival or cell death pathways; (4) the design and execution of screens to assay for FAIM expression and (4) the development of therapeutic protocols involving the use of (i) compounds that regulate FAIM activation and (ii) the establishment of drug and gene therapies for the treatment of various cancer and autoimmune diseases.

E. Formant Of The Invention i. Cell Based Assays

One embodiment of this invention would be to allow for the transfection of cell lines with plasmids containing the wild type or mutant faim genes and then measure the effects of test compounds on apoptosis. The wild type and mutant faim genes could be inserted in many various plasmids to allow for expression in a wide range of cell types. For example, transfected faim has already been shown to block apoptosis in Bal-17 B lymphoma cells. The lack of effect in cells transfected with the FAIM lof mutants would confirm that the compound was effective at the level of FAIM activation or upstream from FAIM activation.

ii. Transgenic Animal Based Assays

One embodiment of this invention would be to generate transgenic animals expressing wild type and mutant faim genes to provide an in vivo assay system for the screening of potential drug candidates. The wild type and mutant faim genes could be inserted in many various plasmids to allow for expression in a wide range of animals or tissue types.

iii. Immunological Based Assays

One embodiment of this invention would be to produce antibodies from peptides generated from the invention. This would allow for immunological blotting assays to test for expression of naturally occurring mutant FAIM in various cell or tissue types, the ability to isolate homologs via immunoprecipitation assays and the ability to purify large quantities of protein from expression systems.

iv. Molecular Biological Based Assays

One embodiment of this invention would be to produce from the invention faim lof and gof RNA and cDNA. This would make it possible to perform a wild range of standard molecular biological assays including, but not limited to, Northern and Southern blotting, PCR, cloning and various screening assays for the detection of intraspecific and interspecific homologs.

v. FAIM Expression Assays

One embodiment of this invention would be to assay for the expression of FAIM in a wide variety of cells including, but not limited to, pathogenic cells. Pathogenic cells would include but not be limited to cancer cells, autoimmune cells and other diseased cells.

DETAILED DESCRIPTION OF PREFERRED EMBODIMENTS

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleic synthesis, and microbial culture and transformation e.g., electroporation, lipofection). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y., which are incorporated herein by reference) which are provided throughout this document. All the information contained therein is incorporated herein by reference.

Oligonucleotides can be synthesized on an applied Bio-Systems oligonucleotide synthesizer [for details see Sinha et al., Nucleic Acids Res. 12:4539 (1984)], according to specifications provided by the manufacture. Complementary oligonucleotides are annealed by heating them to 90° C. in a solution of 10 mM Tris-HCl buffer (pH 8.0) containing NaCl (200 mM) and then allowing them to cool slowly to room temperature.

Assays for detecting the ability of agents to inhibit or enhance FAIM-mediated apoptosis provide for facile high-throughput screening of agent banks (e.g., compound libraries, peptide libraries, and the like) to identify antagonists or agonists. Such FAIM pathway antagonists and agonists may be further developed as potential therapeutics and diagnostic or prognostic tools for diverse types of cancers, autoimmune diseases and hereditary diseases.

1. Screens to Identify Agonists of Antagonists of FAIM

There are several different approaches contemplated by the present invention to confirm the ability of small molecules to specifically inhibit or enhance FAIM activation. One approach is to transfect expression constructs specific for the invention into cells and measure changes in the rate of apoptosis as compared to controls transfected with wild type FAIM after the cells have been exposed to the compound suspected of modulating FAIM activity. Cells may be transiently transfected or stably transfected with the construct under control of an inducible promotor. Furthermore, transgenic animal could be produced allowing for in vivo assays to be conducted.

A. In vitro Assays a. Transfection Assays

Transfection assays allow for a great deal of flexibility in assay development. The wide range of commercially available transfection vectors will permit the expression of the invention in an extensive number of cell types. Additionally, FAIM has been shown to inhibit apoptosis in Bal-17 B lymphoma cells. In one preferred embodiment cells would be transiently transfected with the invention in an expression construct that included an inducible promotor allowing for the initiation of translation and transcription when needed. Cells would be exposed to the agent suspected of modulating FAIM activity, FAIM expression would be turned on and apoptosis would be measured. Rates of apoptosis in cells expressing the invention would be compared to rates of apoptosis in cells transfected with a construct expressing a wild type faim gene and cells expressing an empty expression vector. Rates of apoptosis could be quantitated by any of a number of ways reported in the literature and known to those practiced in the art.

In another preferred embodiment stably transfected cells lines would be developed. The use of an inducible promotor could be utilized in these systems. Screening assays for compounds suspected of modulating FAIM activity would be conducted in the same manner as with the transient transfection assays. Using stably transfected cell lines would allow for greater consistency between experiments and allow for inter-experimental comparisons.

B. In Vivo Assays a. Transgenic Animal Assays

In one embodiment transgenic animals will be constructed using standard protocols. The generation of transgenic animals will allow for the investigation of diseases for which the mutated forms of FAIM may provide the means for determining the physiology of the disease or its treatment.

2. Screens to Identify FAIM Signal Pathway Constituents

A. In vitro Assays

There are several different approaches to identifying FAIM interactive molecules. The invention makes it possible to delineate molecules that may interact with FAIM. Techniques that may be used are, but not limited to, immunoprecipitation of FAIM with antibodies generated to the transcription product of the invention. This would also bring down any associated bound proteins. Another method is to generate fusion proteins containing the wild type form of FAIM connected to a generally recognized pull-down protein such as glutathione S-transferase. Bound proteins can then be eluded and analyzed.

a. Immunoprecipitation

After the generation of antibodies to wild type or mutant FAIM, cells expressing the transfected FAIM are lysed and then incubated with one of the antibodies. Antibodies with the bound FAIM and any associated proteins can then be pulled down with protein-A Sepharose or protein-G Sepharose beads. Antibody bound proteins would then be purified, characterized and sequenced.

b. Fusion Protein Pull-down

A method similar to immunoprecipitation is to construct fusion proteins of the wild type FAIM and glutathione S-transferase (GST). The GST-FAIM fusion proteins are then incubated with cell extracts and then removed with glutathione Sepharose beads. Any bound, FAIM-associated proteins are then characterized.

B. In Vivo Assays a. Yeast Two-hybrid System

The yeast two-hybrid system that identifies the interaction between two proteins by reconstructing active transcription factor dimers. The dimers are formed between two fusion proteins, one of which contains a DNA-binding domain (DB) fused to the first protein of interest (DB-X) and the other, an activation domain (AD) fused to the second protein of interest (AD-Y). The DB-X:AD-Y interaction reconstitutes a functional transcription factor that activates chromosomally-integrated reporter genes driven by promoters containing the relevant DB binding sites. In the present invention FAIM would be the first protein of interest (protein X) and proteins generated from the cDNA libraries would constitute the second protein of interest (protein Y). Large cDNA libraries can be easily screened with the yeast-two hybrid system. Yeast cDNA libraries are commercially available. Standard molecular biological techniques can be employed to isolate and characterize the interacting protein.

3. Screens to Identify FAIM Homologs

Standard molecular biological techniques can be used to identify FAIM homologs. For example, preferred embodiments may included, but are not limited to, DNA-DNA hybridization techniques (e.g. Southern blots) and DNA-RNA hybridization techniques (e.g. Northern blots). Additional techniques may include, for example, immunoscreening of proteins made from library stocks by antibodies generated from the invention.

4. Screens to Assay for FAIM Expression

Standard molecular biological techniques can be used to assay for FAIM expression in normal and pathological cells. FAIM can be immunoprecipitated by antibodies generated from the expression product of the present invention. Additionally, FAIM expression can be assayed by PCR using primers or oligonuceotides generated from the faim gene.

EXPERIMENTAL

The following examples serve to illustrate certain preferred embodiments and aspects of the present invention and are not to be constructed as limiting the scope thereof. In the experimental disclosure which follows, the following methodology apply:

Mice, Male Balb/cByJ mice at 8–14 weeks of age were obtained from The Jackson Laboratory (Bar Harbor, Me.). Mice were housed at least one week prior to experimentation. Mice were cared for and handled at all times in accordance with NIH and institutional guidelines.

B Cell Purification. Splenic B cells from 8 to 12 week old naive Balb/cByJ mice were purified and depleted of T cells and macrophages as previously described (Rothstein et al. "Protection against Fas-dependent Th-l-mediated apoptosis by antigen receptor engagement in B cells" *Nature*

374:163–165, 1995). RBC and non-viable cells were removed by sedimentation over Lymphocyte M (Cedarlane, Ontario, Canada). The resulting B cells were cultured at 37° C. with 5% $CO_2$ in RPMI 1640 medium (Bio Whittaker, Walkersville, Md.) supplemented with 5% heat inactivated fetal bovine serum (Sigma), 10 mM Hepes (pH 7.2), 50 mM 2-ME, 2 mM L-glutamine, 100 U/ml penicillin and 100 mg/ml streptomycin.

Differential Display. Total RNA was prepared from primary murine splenic B cells stimulated with CD40L/CD8a fusion protein crosslinked with anti-CD8 antibody (CD40L) for 48 hours, in the absence or presence of $F(ab')_2$ fragments of polyclonal goat anti-mouse IgM (anti-Ig) added for the final 6 hours of the culture period, using Phenol/GITC (Xie and Rothblum "Rapid, small-scale RNA isolation from tissue culture cells" *Biotechniques* 11:326–327, 1993). Reverse transcription and differential display were performed as described (Liang and Pardee "Differential display of eukaryotic messenger RNA by means of the polymerase chain reaction" *Science* 257:967–971, 1992) using the RNAImage Kit (GenHunter, Brookline, Mass.) Putatively differentially expressed cDNA fragements were excised from dried sequencing gels, eluted in $dH_2O$ and reamplified using the same primer pair originally employed in differential display. These fragments were tested for differential expression by Northern blot; PCR products confirmed by this assay were subcloned into a TA cloning vector (Invitrogen, Carlsbad, Calif.) Plasmid DNA from individual clones was radiolabeled and used to probe additional Northern blots in order to identify the insert responsible for differential expression. Subcloned Northern-positive cDNAs were subjected to automated fluorescent DNA sequencing (Applied Biosystems, Foster City, Calif.) and analyzed by comparison to standard sequencing databases in the public domain (NCBI, BLAST).

Northern Blotting. Total RNA was prepared from primary murine splenic B cells using UltraSpec RNA isolation reagent (Biotecx Laboratories, Houston, Tex.). Purified RNA was electrophoresed on a 1% Agarose/Formaldehyde gel, transferred to GeneScreen Plus (DuPont/NEN, Boston, Mass.) in 10XSSC and hybridized to a 234 bp radiolabeled fragment of faim generated by PCR, employing the primers CTGGATGGCGAGGACCTGAG (5') (SEQ ID NO:13) and GGTGTCACTGAGTGAGCTCTG (3') (SEQ ID NO:14). Initial Northern probing to confirm differential expression was performed as above except that differential display primers were used and the annealing step of PCR was performed for 2 minutes at 40° C. Autoradiography was performed using intensifying screens at −80° C. for 1 to 3 days. A multiple tissue Northern blot was obtained from OriGene Technologies (Rockville, Md.).

cDNA Library Screening. A radiolabeled probe generated as described above was used to screen a directional murine thymic cDNA library constructed in pBKCMV (Stratagene, LaJolla, Calif.). Plaque lifts were performed using Protran membranes (Schleicher and Schuell, Keene, N.H.). A number of individual clones from among $1 \times 10^6$ plaques were sequenced leading to the isolation of a full-length clone as determined by an in-frame stop codon upstream of the start methionine. This clone encodes a novel 179 aa protein as discussed below.

FAIM-specific Antibodies. Two peptides (amino acids 57–58 and 125–138) corresponding to predicted hydrophilic regions of the FAIM ORF and that also fulfilled a number of other characteristic of immunogenic peptides were synthesized by standard techniques. These peptides also contain an N-terminal cysteine followed by an amino-caproic acid. Two mg of each peptide was coupled to KLH (Pierce Chemical, Rockford, Ill.) according to the manufacturer's instructions. The coupled peptides were combined and used to raise anti-peptide antibodies in chickens (Aves Labs, Tigard, Oreg.).

Transfection. Mid-log phase BAL-17 B lymphoma cells in suspension were transfected with 20 mg faim-containing plasmid or pBKCMV empty vector (plus 500 mg carrier salmon sperm DNA) by electroporation at 276V and 550 mF using a Bio-Rad apparatus (Hercules, Calif.). Transfected cells were immediately plated to pre-warmed medium and cultured at 37° C. with 5% $CO_2$ as above (Chu et al. "Electroporation for the efficient transfection of mammalian cells with DNA" *Nuc. Acid Res.* 15:1311–1326, 1987). After 2 days transfected cells were split 1:15 into fresh medium containing 2 mg/ml G418 (Sigma Chemical Company, St. Louis, Mo.) to obtain pools of transfectants. Separately, individual stably transfected clones were isolated by limiting dilution in medium containing G418.

Fas-mediated apoptosis. BAL-17 transfectants stimulated for 24 hours with CD40L were tested as targets in standard 4 hour lectin-dependent $^{51}Cr$ release assays with AE7 CD4+ Th1 effector cells at effector:target cell ratios of 0.3:1–9:1, as previously described (Rothstein et al. "Protection against Fas-dependent Th-1-mediated apoptosis by antigen receptor engagement in B cells" *Nature* 374:163–165, 1995; Foote et al. "Intracellular signaling for inducible antigen receptor-mediated Fas resistance in B cells" *J. Immunol.* 157:1878–1885, 1996), or with Jo-2 anti-Fas antibody (Pharmingen, San Diego, Calif.) at 50, 5, or 0.5 ng/ml. Alternatively, nuclei obtained from CD40L-stimulated BAL-17 transfectants were stained with propidium iodide and the level of subdiploid DNA determined by flow cytometry, essentially as described (Nicoletti et al. "A rapid and simple method for measuring thymocyte apoptosis by propidium iodide staining and flow cytometry" *J. Immunol. Methods* 139:271–279, 1991).

PARP cleavage. B cell protein lysates were resolved by 15% SDS-PAGE, transferred to Hybond nitrocellulose membranes (Amersham, Arlington Heights, Ill.) and blocked with 5% non-fat dry mile in TBS-T for 1 hour at room temperature. Membranes were probed with anti-PARP antibody 2-C-10 (Calbiochem, San Diego, Calif.) at 1:500 in TBS-T. After washing blots were incubated with horseradish peroxidase (HRP)-conjugated goat anti-mouse IgG and developed by enhanced chemiluminescence (Dupont/NEN), as descried (Karras et al. "Antigen-receptor engagement in B cells induces nuclear expression of STAT5 and STAT6 proteins that bind and transactivate an IFN-g activation site" *J. Immunol.* 157:39–47, 1996).

Fas expression. B cells were stained with phycoerythrin-conjugated Jo2 Fas-specific antibody or anti-TNP isotype control antibody (Pharmingen) in the presence of 2% normal rabbit serum and 2.4G2 (anti-FcR) antibody, as previously described (Foote et al. "IL-4 induces Fas resistance in B cells" *J. Immunol.* 157:2749–2753, 1996). Relative fluroescence intensity was detected by flow cytometry with a FACScan instrument (Becton Dickinson, Sunnyvale, Calif.).

FAIM expression. Two peptides (amino acids 57–68 and 125–138) corresponding to predicted hydrophilic regions of the FAIM ORF (Kyte and Doolittle "A simple method for displaying the hydropathic character of a protein" *J. Mol. Biol.* 157:105–132, 1982) were synthesized by Research Genetics Corporation (Huntsville, Ala.). These peptides contain an N-terminal cysteine followed by an amino-caproic acid. Each peptide (2 mg) was separately coupled to KLH (Pierce Chemical, Rockford, Ill.); the coupled peptides were combined and used to generate anti-FAIM peptide antibodies in chickens (Aves Labs, Tigard, Oreg.). B cell protein lysates were resolved by 15% SDS-PAGE, transferred to Hybond nitrocellulose membranes (Amersham, Arlington Heights, Ill.) and blocked with 10% Blok-Hen blocking reagent (Aves Labs) for 1 hour at room temperature. The nitrocellulose filters were then probed with FAIM-specific antibodies diluted 1:1000 in TBS-T containing 10% Block-Hen, for 1.5 hours at room temperature. After washing, blots were incubated with horseradish peroxidase (HRP) conjugated goat anti-chicken IgY (Aves Labs) for 1 hour and developed by enhanced chemiluminescence (Dupont/NEN) as described (31).

Reagents. Affinity purified F(ab')$_2$ fragments of polyclonal goat anti-mouse IgM were obtained from Jackson ImmunoResearch Laboratories (West Grove, Pa.) and used at 10 mg/ml. Soluble rCD40L was obtained from transfected J558L cells that secrete a chimeric CD40L/CD8a fusion protein (Lane et al. "Soluble CD40 ligand can replace the normal T cell-derived CD40 ligand signal to B cells in T cell-dependent activation" *J. Exp. Med.* 177:1209–1213, 1993), which was collected and dialyzed against 25,000 molecular weight cut-off dialysis tubing, as previously described (Francis et al. "Induction of the transcription factors NF-κB. AP-1 and NF-AT during B cell stimulation through the CD40 receptor" receptor" *Intl. Immunol.* 7:151–161, 1995). A similarly dialyzed supernatant containing anti-CD8 antibody from the 53-6-72 hybridoma was used to crosslink the fusion protein. CD40L and anti-CD8 containing supernatants were used at final dilutions of 1:10 and 1:80, respectively. G418 was obtained from Gibco/BRL (Gaithersburg, Md.). An EST encompassing putative human FAIM was obtained from the I.M.A.G.E. consortium (Lennon et al. "The I.M.A.G.E. consortium: an integrated molecular analysis of genomes and their expression" *Genomics* 33:151–152, 1996). $^{51}$Cr was obtained from Dupont/NEN.

EXPERIMENT 1

In previous work we showed that B cell treatment with anti-Ig for only the final 1–12 hours of a 48 hour culture with CD40L produced a time-dependent increase in Fas-resistance that was abrogated by cycloheximide (Foote et al. "Intracellular signaling for inducible antigen receptor-mediated Fas resistance in B cells" *J. Immunol.* 157:1878–1885, 1996). Additional experiments demonstrated that the induction of Fas-resistance in CD40L-stimulated B cells by anti-Ig treatment for 6 hours was completely blocked by the addition of actinomycin D (data not shown). These results strongly suggest that transcriptional activation and gene expression are required for the receptor-specific induction of the Fas-resistant state. For this reason, genes that oppose Fas-mediated apoptosis might be captured by identifying transcripts expressed uniquely in Fas-resistant B cells.

To identify genes expressed coordinately with the induction of Fas-resistance, we employed a differential display strategy (Liang and Pardee "Differential display of eukaryotic messenger RNA by means of the polymerase chain reaction" *Science* 257:967–971, 1992). RNA was extracted from B cells stimulated with CD40L alone for 48 hours (Fas-sensitive) and from B cells stimulated with CD40L (for 48 hours) plus anti-IgM for the final 6 hours of culture (Fas-resistant), and was reverse-transcribed. Application of arbitrary decameric primer pairs to these cDNA populations permitted reproducible amplification of a number of transcripts present in Fas-resistant B cells but absent in their Fas-sensitive counterparts. These amplified gene fragments were excised and used as probes in Northern blots of RNA obtained from Fas-sensitive and Fas-resistant primary B cells to confirm differential expression (FIG. 1a). Of 40 such fragments, 8 failed to reamplify. Of the remaining 32, 8 displayed differential expression by Northern blotting. One of these recognized an approximately 1.2 kb transcript on Northern blot (FIG. 1a) that was widely expressed in multiple tissues, with the highest levels present in murine brain, thymus, kidney and spleen (FIG. 1b). This transcript was chosen for further analysis.

EXPERIMENT II

Using a radiolabeled probe generated by PCR, a murine thymic cDNA library was screened and the DNA from positive plaques sequenced. A number of overlapping clones were identified whose consensus sequence was approximately 1.2 kb, consistent with the expression data described above. Subsequently a full-length clone was identified that contained an in-frame STOP codon upstream of the START methionine, and possessed, in the 3' UTR, an RNA instability motif, poly A+ consensus motifs and a poly A+ tail (Malter "Identification of an AUUUA-specific messenger RNA binding protein" *Science* 246:664–666, 1989). This cDNA appeared to encode a novel 179 amino acid open reading frame (FIG. 2). Structural analysis predicted a b-strand-rich, stable, soluble protein with a slightly acidic pl (pH 5.4). No substantial regions of homology with any other sequence are present.

EXPERIMENT III

Figure 3:
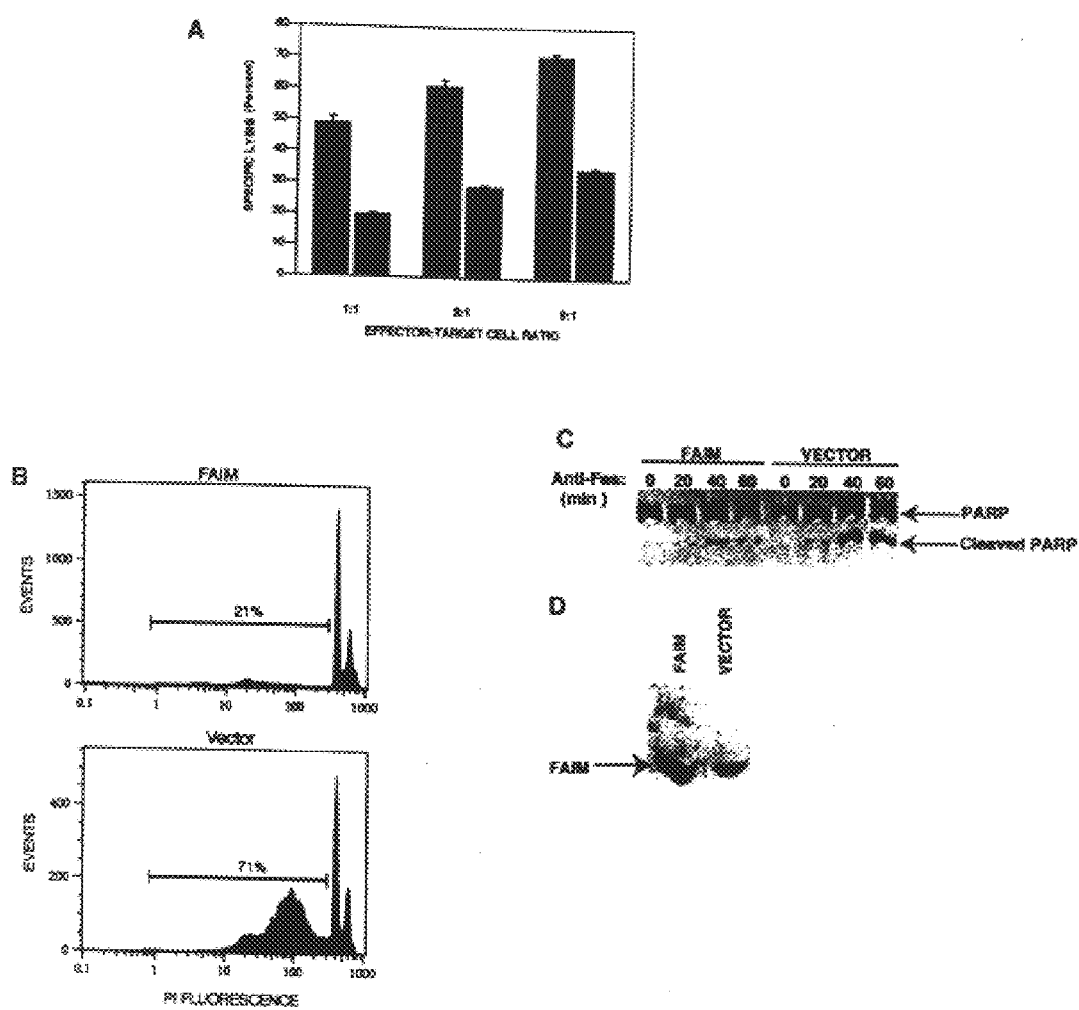
FIG. 3 shows the modulation of Fas-mediated apoptosis in BAL-17 B cells transfected with faim. (A) The results of a mixed lymphocyte reaction at various effector:target cell ratios. (B) Cell death analysis using propidium iodide of faim transfected and vector transfected BAL-17 B lymphocytes. (C) PARP cleavage in faim or vector transfected BAL-17 B lymphoma cells. (D) Western blots showing FAIM expression in faim and vector transfected BAL-17 B lymphoma cells.

To determine the capacity of the isolated cDNA clone to produce resistance to Fas-mediated apoptosis, BAL-17 murine B lymphoma cells were transfected with the pBKCMV expression vector. BAL-17 cells were chosen because their activation responses mimic primary B cells in a variety of ways and they are readily transfectable (Chiles et al. "Cross-linking of surface Ig receptors on murine B lymphocytes simulates the expression of nuclear tetradecanoyl phorbol acetate-response element binding-proteins" *J. Immunol.* 146:1730–1735, 1991; Mizuguchi et al. "Protein kinase C activation blocks anti-IgM-mediated signaling in BAL-17 B lymphoma cells" *J. Immunol.* 139:1054–1059, 1987; Seyfert et al. "Egr-1 expression in surface Ig-mediated B cell activation:kinetics and association with protein kinase C activation" *J. Immunol.* 145:3547–3553, 1990). Like primary B cells, unstimulated BAL-17 B cells express little Fas, but treatment with CD40L induces Fas expression and sensitivity to Fas-mediated apoptosis (data not shown). Following electroporation, pools of BAL-17 B cells stably transfected with either full-length cDNA or empty vector were selected in G418 for 2 weeks. These two populations differed in their susceptibility to Fas-killing induced by FasL-bearing Th1 effector cells: at each effector:target cell ratio tested, specific lysis of cDNA-transfected BAL-17 B cells, detected by chromium release assay, was reduced by half or more in comparison to cells transfected with vector alone (FIG. 3a), despite equivalent levels of surface Fas expression (data not shown). These results suggest a level of protection of 9-fold or more, in terms of the effector:target ratio required to produce equivalent levels of apoptosis in FAIM- and vector-transfected BAL-17 B cells. The reduction in Fas-killing was also apparent when cytotoxicity was induced by lytic Jo-2 anti-Fas antibody (data not shown). In addition, stably transfected clones were isolated by limiting dilution and tested for susceptibility to Fas killing. The results obtained with individual clones completely mimicked those obtained with G418-resistant pools in that Fas-mediated apoptosis (produced by Jo-2) was reduced by ½ to ⅔ in stably transfected cDNA-expressing BAL-17 B cells in comparison to BAL-17 cells transfected with empty vector, as detected by propidium iodide staining for subdiploid DNA (FIG. 3b). These data indicate that the novel cDNA transcript initially identified in inducibly Fas-resistant B cells codes for a Fas Apoptosis Inhibitory Molecule (FAIM) that counteracts Fas signaling for cell death when overexpressed.

EXPERIMENT IV

To characterize the nature of the FAIM-induced block in Fas signaling for cell death, the fate of poly-ADP ribose polymerase (PARP), a terminal caspase cleavage product, was examined by Western blotting size-separated whole cell extracts (Tewari et al. "Yama/CPP32 beta, a mammalian homolog of CED-3, is a CrmA-inhibitable protease that cleaves the death substrate poly(ADP-ribose) polymerase" Cell 81:801–809, 1995). Proteolytic fragments of PARP were readily detected when vector-transfected BAL-17 B cells were treated for 40 minutes with Jo-2 anti-Fas antibody. In contrast, there was little or not PARP cleavage in faim-transfected BAL-17 B cells up to 60 minutes after anti-Fas treatment (FIG. 3c). Thus, FAIM blocks Fas-apoptosis at a step proximal to the cleavage of the caspase substrate, PARP.

As a control for these experiments, FAIM expression in faim-transfected and vector-transfected BAL-17 B cells was determined by Western blotting with polyclonal anti-FAIM antibody. Antibody was prepared by immunizing chickens with 2 relatively hydrophilc peptides derived the FAIM sequence (amino acids 57–68, DGKEEIRREWMF (SEQ ID NO:15); and 125–138, RLDGEDLRVVLEKD (SEQ ID NO:16)) coupled to KLH; the resultant antibody (purified from the IgY fraction of egg yolks) specifically recognized a protein of the expected size, about 20 kDa, on Western blot whereas pre-immune IgY did not. Using this antibody the expression of FAIM protein was found to be much increased in faim-transfected, as opposed to vector-transfected, BAL-17 B cells (FIG. 3c).

EXPERIMENT V

To further evaluate the association between FAIM expression and inducible Fas-resistance, primary B cells were studied by Northern and Western blotting after stimulation with CD40L and anti-Ig. CD40L stimulation alone, which induces Fas expression and Fas-sensitivity, elicited little or no increase in faim expression over the low basal level present in unstimulated B cells. However, additon of anti-IgM, which induces Fas-resistance, to CD40L-stimulated B cells produced a marked, time-dependent increase in faim mRNA, beginning at 1 hour and reaching a maximum after 6 hours of anti-lg treatment (FIG. 4a). Similar results were obtained when the expression of FAIM protein was monitored. FAIM was absent in unstimulated B cells and B cells stimulated for 48 hours with CD40L alone: however, addition of anti-IgM to CD40L-stimulated B cells produced a marked increase in FAIM protein, first seen after 18 hours of anti-Ig treatment (FIG. 4b). In some experiments FAIM protein expression was detected after 6 hours of anti-Ig treatment (data not shown).

The correlation between sIg-induced FAIM expression and Fas-resistant was tested further by examining tolerant, autoreactive B cells obtained from double transgenic, anti-HEL/HEL mice. In these B cells, in vitro studies showed that specific antigen (sHEL) is an insufficient stimulus to produce Fas-resistance, whereas Fas-resistance is induced by more extensive sIg crosslinking with anti-Ig (Foote et al. "Tolerant B lymphocytes acquire resistance to Fas-mediated apoptosis after treatment with interleukin 4 but not after treatment with specific antigen unless a surface immunoglobulin threshold is exceeded" J. Exp. Med. 187:847–853, 1998). In keeping with this, sHEL failed to induce upregulation of FAIM protein expression in B cells drawn from double transgenic anti-HEL/HEL mice, whereas FAIM protein was induced by anti-Ig in these B cells (FIG. 4c). In this situation, as with anti-Ig-treated B cells from normal mice, above, induction of FAIM expression correlates with production of Fas-resistance.

EXPERIMENT VI

To evaluate the possibility that faim is phylogenetically conserved, public databases were searched for evidence of similar genes in other species. Human faim was obtained by identifying a consensus sequence from overlapping human ESTs with homology to mouse faim, followed by sequencing of a single EST clone that completely spanned putative human faim (Lennon et al. "The I.M.A.G.E. consortium: an integrated molecular analysis of genomes and their expression" Genomics 33:151–152). The consensus/EST sequence was used to predict an amino acid sequence, which showed human FAIM to be 90% identical to the predicted amino acid sequence of mouse FAIM (data not shown). These results are complemented by Southern analysis of genomic DNA showing hybridization by a mouse faim probe to all mammalian species tested (human, monkey, rat, mouse, dog, cow, and rabbit; data not shown).

C. elegans FAIM was obtained by amplifying cDNA with primers based on the predicted exon structure of a random genomic sequence of unknown function, and then sequencing the resultant DNA. The predicted amino acid sequence of this C. elegans FAIM is 50% identical to the predicted amino acid sequence of mouse FAIM (data not shown). The extensive evolutionary conservation manifest in the sequences of human, mouse and C. elegans faim strongly suggests that the faim gene produce is a key apoptotic regulatory molecule that has been retained with minimal change throughout phylogeny.

From the above it should be clear that the present invention provides a wide variety of reagents and methodologies that allow for the identification and testing of agonists and antagonists of cell survival pathways. In particular, the present invention provides a wide variety of ways to screen for compounds that can modulate Faim activity and, therefore, can regulate cellular apoptosis. The means of identifying such compounds (now provided by the present invention) would permit the development of diagnostic and therapeutic procedures for the treatment of various cancers and neurological diseases. Additionally, screens for Faim intra- and interspecific homologs as well as Faim associated binding molecules are possible as a result of this invention. Furthermore, this invention makes possible the construction of cells and organisms that are made deficient in expression of this gene or made to express additional copies of this gene.

We claim:

1. A purified composition comprising a DNA molecule having the polynucleotide sequence set fourth in SEQ ID NO:1.

2. Isolated RNA transcribed from the DNA of claim 1.

3. An expression construct comprising the DNA of claim 1.

4. Isolated cells comprising the expression construct of claim 3.

5. A primer for generating an oligonucleotide of SEQ ID NO:1 consisting of 12 to 18 base pairs of SEQ ID NO:1.

* * * * *